United States Patent
Zhao et al.

(10) Patent No.: US 11,883,477 B2
(45) Date of Patent: Jan. 30, 2024

(54) **TRIPLE VACCINE FOR DISEASES CAUSED BY *SALMONELLA TYPHIMURIUM*, *RIEMERELLA ANATIPESTIFER* AND *ESCHERICHIA COLI***

(71) Applicant: Qingdao Bolin Biological Technology Co., Ltd., Qingdao (CN)

(72) Inventors: Yongda Zhao, Qingdao (CN); Lili Guo, Qingdao (CN); Lihua Ma, Qingdao (CN)

(73) Assignee: Qingdao Bolin Biological Technology Co., Ltd., Qingdao (CN)

( * ) Notice: Subject to any disclaimer, the term of this patent is extended or adjusted under 35 U.S.C. 154(b) by 56 days.

(21) Appl. No.: 17/532,217

(22) Filed: Nov. 22, 2021

(65) Prior Publication Data

US 2022/0193214 A1 Jun. 23, 2022

(30) Foreign Application Priority Data

Nov. 21, 2020 (CN) .......................... 202011315483.6

(51) Int. Cl.
| | |
|---|---|
| *A61K 39/112* | (2006.01) |
| *A61P 31/04* | (2006.01) |
| *A61K 39/02* | (2006.01) |
| *A61K 39/108* | (2006.01) |
| *A61K 39/00* | (2006.01) |

(52) U.S. Cl.
CPC ...... *A61K 39/0275* (2013.01); *A61K 39/0208* (2013.01); *A61K 39/0258* (2013.01); *A61P 31/04* (2018.01); *A61K 2039/521* (2013.01); *A61K 2039/70* (2013.01)

(58) Field of Classification Search
None
See application file for complete search history.

*Primary Examiner* — Jana A Hines
*Assistant Examiner* — Khatol S Shahnan Shah
(74) *Attorney, Agent, or Firm* — Fox Rothschild LLP

(57) ABSTRACT

The present disclosure belongs to the technical field of veterinary biological products, and specifically relates to a triple vaccine for diseases caused by *Salmonella typhimurium*, *Riemerella anatipestifer* and *Escherichia coli*. In the triple vaccine, antigens are an inactivated *Salmonella typhimurium* S01 strain, an inactivated *Riemerella anatipestifer* R01 strain and an inactivated *Escherichia coli* E01 strain. The three strains used in the vaccine have high virulence, disable immunogenicity and disable cross-protection. The prepared vaccine has a desirable safety, causing no local or systemic adverse reactions. In a shelf life test, all indicators of the vaccine are stable and effective after a data analysis of traits, a safety test and an efficacy test; in addition, efficacy test results prove that the inactivated triple vaccine can produce desirable antibodies and relatively desirable attacking protection.

3 Claims, No Drawings
Specification includes a Sequence Listing.

TRIPLE VACCINE FOR DISEASES CAUSED BY SALMONELLA TYPHIMURIUM, RIEMERELLA ANATIPESTIFER AND ESCHERICHIA COLI

CROSS REFERENCE TO RELATED APPLICATION(S)

This patent application claims the benefit and priority of Chinese Patent Application No. 202011315483.6, filed on Nov. 21, 2020, the disclosure of which is incorporated by reference herein in its entirety as part of the present application.

REFERENCE TO SEQUENCE LISTING SUBMITTED ELECTRONICALLY

This application contains a sequence listing, which is submitted electronically via EFS-Web as an ASCII formatted sequence listing with a file name "199190-00015_Seq-Listing" and a creation date of Aug. 29, 2023, and having a size of 1.08 kb. The sequence listing submitted via EFS-Web is part of the specification and is herein incorporated by reference in its entirety.

TECHNICAL FIELD

The present disclosure belongs to the technical field of veterinary biological products, and specifically relates to a triple vaccine for diseases caused by *Salmonella typhimurium*, *Riemerella anatipestifer* and *Escherichia coli*.

BACKGROUND ART

*Salmonella typhimurium*, as an important pathogen for zoonosis, has a wide host range and can cause various acute or chronic infectious diseases in humans and animals. *Salmonella typhimurium* from animal sources poses a serious threat to livestock breeding and human health, and has important public health significances. Antibacterial drugs are important for treating *Salmonella typhimurium* infection, but abuse and misuse of the antibacterial drugs has led to severe drug resistance. Past data show that 90% of antibiotics are annually used in food animals in the world, making animals an important reservoir host for drug-resistant bacteria. Moreover, the drug-resistant bacteria and original drug-resistant genes are spreading across species from animals or the environment to humans. Therefore, vaccines are very important in controlling *salmonellosis*.

*Riemerella anatipestifer* can infect poultry such as ducks, geese and turkeys to bring bacterial diseases that are common in large-scale waterfowl breeding, generally causing serious economic losses. The *Riemerella anatipestifer* mainly affects ducklings and young geese at the age of 2-7 weeks, bringing characteristic lesions such as fibrinous pericarditis, perihepatitis, air sacculitis, arthritis, salpingitis and meningitis, causing serious economic losses to duck farms.

*Escherichia coli* can cause *Escherichia coli* disease, a common bacterial disease in farm production that can be infected by ducks of all ages, with loss of appetite, diarrhea, weight loss and low production performance as characteristic of clinical manifestations. The disease can also occur in chickens of all ages, with varying incidence rate and mortality. Once occurring, the disease can spread rapidly throughout chicken flocks. The disease has no obvious seasonality and can occur in all seasons. The incidence rate and mortality of chicks are higher than those of adult chicken. In addition, the disease can be induced by stress factors such as uneven feed nutrition, poor breeding environment in farms, large differences in temperature and humidity in chicken houses and sudden change of feed.

At present, due to annually increasing amount in breeding, the duck has become important poultry in China, while the above three diseases are becoming more and more serious to the duck farms. Therefore, it is urgent to conduct systematic research on the prevalence of the *Salmonella typhimurium*, the *Riemerella anatipestifer* and the *Escherichia coli* in Chinese farms. There is further an urgent need to develop an inactivated triple vaccine against the *Salmonella typhimurium*, the *Riemerella anatipestifer* and the *Escherichia coli*, to avoid harms caused by the three diseases to the breeding industry.

SUMMARY

A technical problem to be solved by the present disclosure is to provide an inactivated triple vaccine for diseases caused by *Salmonella typhimurium*, *Riemerella anatipestifer* and *Escherichia coli*, to avoid harms caused by the diseases of the three bacteria to the breeding industry.

To solve the above problem, the present disclosure is implemented by the following technical solutions: A *Salmonella typhimurium* S01 strain was deposited in the China Center for Type Culture Collection (CCTCC) in Wuhan University, Wuhan City, China (address: Luojia Hills, Bayi Road, Wuchang District, Wuhan City, Hubei Province) on Sep. 18, 2020 with a deposit number of CCTCC No. M2020515.

An *Escherichia coli* E01 strain was deposited in the CCTCC in Wuhan University, Wuhan City, China (address: Luojia Hills, Bayi Road, Wuchang District, Wuhan City, Hubei Province) on Sep. 18, 2020 with a deposit number of CCTCC No. M2020514.

A *Riemerella anatipestifer* R01 strain was deposited in the CCTCC in Wuhan University, Wuhan City, China (address: Luojia Hills, Bayi Road, Wuchang District, Wuhan City, Hubei Province) on Sep. 18, 2020 with a deposit number of CCTCC No. M2020516.

A second technical problem to be solved by the present disclosure is to provide use of the three strains.

To solve the above problem, the present disclosure is implemented by the following technical solutions: An inactivated triple vaccine is provided for diseases caused by *Salmonella typhimurium*, *Riemerella anatipestifer* and *Escherichia coli*, where antigens are an inactivated *Salmonella typhimurium* S01 strain, an inactivated *Riemerella anatipestifer* R01 strain and an inactivated *Escherichia coli* E01 strain.

Further, the antigens may be inactivated by formaldehyde, and viable counts before inactivation may be all $9 \times 10^9$ colony forming unit (CFU)/ml.

Further, a preparation method of the inactivated triple vaccine may include the following steps:
1) antigen preparation: resuspending bacterial sludges of antigens of purely qualified S01, R01 and E01 strains in a proper amount of sterilized physiological saline, conducting dilution to $9.0 \times 10^9$ CFU/ml and inactivation; after passing quality inspection, mixing the three antigens at a volume ratio of 1:1:1 to obtain a mixed antigen for later use;
2) adjuvant preparation: treating a Montanide GEL 02 adjuvant at 121° C. and a high pressure for 15 min for later use;

3) mixing the mixed antigen with the Montanide GEL 02 at a ratio of 5:95, and stirring at a low speed evenly with a mixer; and 4) sub-packaging: sub-packaging a mixture obtained in step 3) quantitatively, sealing by caps, labeling and storing at 2-8° C.

Further, the inactivated triple vaccine may be subjected to inspection of traits, sterility, safety and efficacy.

The present disclosure has the following beneficial effects.

The *Salmonella typhimurium* S01 strain, the *Riemerella anatipestifer* R01 strain and the *Escherichia coli* E01 strain used in the vaccine have high virulence, disable immunogenicity and disable cross-protection. The prepared vaccine has a desirable safety, causing no local or systemic adverse reactions. In a shelf life test, all indicators of the vaccine are stable and effective after a data analysis of traits, a safety test and an efficacy test; in addition, efficacy test results prove that the inactivated triple vaccine can produce desirable antibodies and relatively desirable attacking protection.

DETAILED DESCRIPTION OF THE EMBODIMENTS

In order to make the objectives, technical solutions, and advantages of the examples of the present disclosure clearer, the technical solutions in the examples of the present disclosure are described clearly and completely below. Apparently, the described examples are some rather than all of the examples of the present disclosure. All other embodiments obtained by a person of ordinary skill in the art on the basis of the embodiments of the present invention without creative efforts shall fall within the protection scope of the present invention.

A *Salmonella typhimurium* strain, a *Riemerella anatipestifer* strain and an *Escherichia coli* strain are selected in combination to prepare an inactivated triple vaccine of the present disclosure. The present disclosure is described in detail below with reference to the accompanying drawings and examples.

Example 1: Information of a *Salmonella typhimurium* S01 Strain

1. Epidemiological investigation: since 2017, the epidemiology of *Salmonella typhimurium* had been investigated, and some duck farms had been subjected to follow-up survey. The results of the investigation shows that the *Salmonella typhimurium* is now widely present in duck farms in China.

2. Bacterial isolation: disease materials such as lungs, heart, liver, intestines and fecal swabs of suspected dead ducks were collected. Sample collection and separation methods were mainly based on national standards (GB 4789.4-2016). A surface of disease materials was disinfected with 75% alcohol, organs were collected aseptically and cut into pieces, placed in a sterile homogenization bag with buffered peptone water (BPW), and culture was conducted at 37° C. and 150 r/min for 8 h for pre-enrichment culture; 1 mL of an enrichment culture solution was placed in 10 mL of a TTB at 42° C. for 20-24 h for selective enrichment culture, and 10 μL of a selective enrichment culture solution was dipped with an inoculating loop to streak on an XLT4 agar plate into three regions, and incubation was conducted at 37° C. for 24 h; a needle tip-sized single colony with a round, colorless and transparent appearance and a neat edge, or a typical colony with a black center and transparent edge on the XLT4 plate was selected and transferred to a *Salmonella* chromogenic plate for culture at 37° C. for 24 h; suspected *Salmonella typhimurium* isolates showed purple on the *Salmonella* chromogenic plate, and further identification was conducted.

3. Bacteria identification 3.1. Observation of morphology: the suspected colony was smeared and subjected to Gram staining microscopic examination to observe the morphology of the bacteria.

3.2. Identification of biochemical characteristics: according to the instructions of biochemical reagents, pure cultures or bacterial suspensions of isolates were inoculated into various biochemical identification tubes as required; cultivation was conducted statically in a biochemical incubator at 37° C., and isolates that meet the biochemical characteristics of *Salmonella typhimurium* were transferred to an XLT4 agar plate for purification culture.

3.3. PCR identification: the bacteria initially identified above were further determined by PCR. A few colonies to be tested were mixed in 100 μL of a sterile PBS using an inoculating loop, and 1 μL of a bacterial suspension was used as a PCR template. According to a primer sequence of a *Salmonella typhimurium* invA gene, P1: 5'-TCGCACCGT-CAAAGGAACCGTAAAGC-3' (SEQ ID NO: 1), and P2: 5'-GCATTATCGATCAGTACCAGCC GTCT-3' (SEQ ID NO: 2), an amplified fragment had a size of 331 bp, where the primers were synthesized by Sangon Biotech (Shanghai) Co., Ltd.

3.4. Serotyping: the *Salmonella typhimurium* isolated and identified was serotyped using a *Salmonella* serum kit. The results show that the *Salmonella typhimurium* had the largest content.

4. Virulence test: 20 strains of *Salmonella typhimurium* isolated and identified were injected intramuscularly into 10 21-day-old cherry valley ducks, 0.5 ml for each duck; another 10 ducks free of challenging experiment were used as a control. The death of ducks were observed and recorded. The test results show that the S01 strain has the highest virulence, and all 10 ducks die within 14 d. The *Salmonella typhimurium* was isolated from a liver of laying ducks in a duck breeding farm in Weifang, Shandong on Oct. 9, 2019.

5. Immunogenicity: according to results of the virulence test, bacteria solutions of S01 strains with a relatively high virulence were adjusted to $1.0 \times 10^9$ CFU/ml, and inactived by formaldehyde to obtain antigens; the antigens were mixed with a Montanide GEL 02 adjuvant at a volume ratio of 95:5 for emulsification to prepare monovalent inactivated vaccines; and each vaccine was injected intramuscularly with 7-day-old cherry valley ducks, at an injection volume of 0.5 ml/duck, and 10 ducks for each group. On the 21st day after immunization, blood was collected and serum was isolated, and an antibody titer of the serum was determined by a microagglutination test method; the strain was used for challenge experiment on the leg muscle by intramuscular injection (a viable count was about $1.0 \times 10^8$ CFU). The incidence and death of experimental ducks were observed. The antibody test results show that the immunized group 5/5 is ≥1:32, and the control group 5/5 is ≤1:4; the results of challenge protection efficiency show that the immunized group 5/5 is protected, and the control group 5/5 is diseased.

6. Cross-challenge protection: according to results of the virulence test, bacteria solutions of S01 strain isolates were adjusted to $1.0 \times 10^9$ CFU/ml, and inactivated by formaldehyde to obtain antigens; the antigens were mixed with a Montanide GEL 02 adjuvant at a volume ratio of 95:5 for emulsification to prepare monovalent inactivated vaccines; and each vaccine was injected intramuscularly with 7-day-old cherry valley ducks, at an injection volume of 0.5 ml/duck, and 10 ducks for each group. On the 21st day after immunization, *Salmonella enteritidis* and *Salmonella* delpy were used for challenge experiment on the leg muscle by intramuscular injection (a viable count was about $1.0\times10^8$ CFU). The incidence and death of experimental ducks were observed. The test results show that none of the ducks in the immunized group is diseased or died, and all ducks show 5/5 protection; while all ducks in the control group show 5/5 incidence. This shows that the inactivated vaccine prepared with the S01 strain can resist the attack of the *Salmonella enteritidis* and *Salmonella* delpy for protection.

Example 2: Information of a *Riemerella anatipestifer* R01 Strain

1. Epidemiological investigation: since 2017, the epidemiology of *Riemerella anatipestifer* had been investigated, and some duck farms had been subjected to follow-up survey. The results of the investigation shows that the *Riemerella anatipestifer* is now widely present in duck farms in China.

2. Isolation and identification: a tumor-specific antigen (TSA) medium (containing 0.01% nicotinamide adenine dinucleotide (NAD) and 5% calf serum) was inoculated into a suspected disease material, and incubation was conducted at 37° C. for 24-48 h; suspected colonies were selected using 16S rRNA PCR for identification (F: ACTTCAGGTACCCCCAGCTT (SEQ ID NO: 3); R: GTGCCGTGAGGTGTTAGGTT (SEQ ID NO: 4); 364 bp); and a total of 43 strains of *Riemerella anatipestifer* were isolated.

3. Morphology and biochemical characteristics: the *Riemerella anatipestifer* formed round, slightly-protruding, and creamy small colonies with a smooth surface on the TSA medium (being observed under light, the colonies appeared light blue). Gram staining microscopic examination showed scattered or a few of paired Gram-negative brevibacterium or coccobacillus. The colonies all showed negative in lactose fermentation test, galactose fermentation test, methyl red test, VP test, hydrogen sulfide production test, nitrate reduction test and citrate test, and no hydrogen sulfide was produced; and the colonies all showed positive in oxidase test and catalase test, which was basically in line with the biochemical characteristics of RA.

4. Cultivation characteristics: the *Riemerella anatipestifer* showed uniform turbid growth in a tryptone soy broth liquid medium containing 0.01% coenzyme (NAD) and 5% newborn calf serum; cultivation was conducted on the tryptone soy agar solid medium containing 0.01% NAD and 5% newborn calf serum at 37° C. for 24-48 h to form a round, smooth, moist, colorless and transparent dewdrop-like colony with a diameter of 0.3-2.0 mm.

5. Serotype identification: serotype identification was conducted using a plate agglutination test, where a *Riemerella anatipestifer* type 2 was the majority, followed by a type 1 and a type 4.

6. Strain virulence test: 14 strains of *Riemerella anatipestifer* type 2 isolated and identified were injected intramuscularly into 10 21-day-old cherry valley ducks, 0.5 ml for each duck; another 10 ducks free of challenging experiment were used as a control. The death of ducks was observed and recorded. The test results show that the R01 strain has the highest virulence, and all ducks die within 14 d. The *Riemerella anatipestifer* was isolated from a liver of cherry valley ducks in Kaifeng, Henan Province on Mar. 15, 2019.

7. Immunogenicity: bacteria solutions of R01 strains were adjusted to $1.0\times10^9$ CFU/ml, and inactivated by formaldehyde to obtain antigens; the antigens were mixed with a Montanide GEL 02 adjuvant at a volume ratio of 95:5 for emulsification to prepare monovalent inactivated vaccines; and each vaccine was injected intramuscularly with 7-day-old cherry valley ducks, at an injection volume of 0.5 ml/duck, and 10 ducks for each group. On the 21st day after immunization, blood was collected and serum was isolated, and an antibody titer of the serum was determined by a microagglutination test method; the strain was used for challenge experiment on the leg muscle by intramuscular injection (a viable count was about $1.0\times10^7$ CFU). The incidence and death of experimental ducks were observed. The antibody test results show that the immunized group 5/5 is greater than or equal to 1:32, and the control group 5/5 is less than or equal to 1:4; the results of challenge protection efficiency show that the immunized group 5/5 shows protection, and the control group 5/5 shows incidence.

Example 3: Information of an *Escherichia coli* Strain E01

1. Epidemiological investigation: since 2017, the epidemiology of *Escherichia coli* had been investigated, and some duck farms had been subjected to follow-up survey. The results of the investigation shows that the *Escherichia coli* is now widely present in duck farms in China.

2. Isolation and identification: suspected organs or anal swabs of ducks were added to a LB medium for incubation at 37° C. for 16-20 h; a bacteria solution was dipped using an inoculating loop to conduct streak inoculation on a MacConkey agar, and incubation was conducted at 37° C. for 16-20 h; colonies were selected for inoculation on an Eosin-Methylene Blue plate, and incubation was conducted at 37° C. for 16-20 h.

3. Morphology and biochemical characteristics: on the MacConkey agar, the *Escherichia coli* has round, bright pink or deep pink colonies, with a neat edge and a smooth surface; meanwhile, on the Eosin-Methylene Blue agar, the *Escherichia coli* has round, deep purple or black colonies, with a smooth surface showing metallic luster.

4. Serotype identification: the serotype was identified as O78.

5. Strain virulence test: 10 strains of *Escherichia coli* O78 isolated and identified were injected intramuscularly into 10 21-day-old cherry valley ducks, 0.5 ml for each duck; another 10 ducks free of challenging experiment were used as a control. The death of ducks were observed and recorded. The test results show that the E01 strain has the highest virulence, and all 10 ducks die within 5 d. The *Riemerella anatipestifer* was isolated from a liver of cherry valley ducks in Kaifeng, Henan Province on Mar. 15, 2019. The *Escherichia coli* was isolated from duck intestines at a duck farm in Foshan, Guangzhou on Jul. 4, 2019.

6. Immunogenicity: bacteria solutions of E01 strains were adjusted to $1.0\times10^9$ CFU/ml, and inactivated by formaldehyde to obtain antigens; the antigens were mixed with a Montanide GEL 02 adjuvant at a volume ratio of 95:5 for emulsification to prepare monovalent inactivated vaccines; and each vaccine was injected intramuscularly with 7-day-old cherry valley ducks, at an injection volume of 0.5 ml/duck, and 10 ducks for each group. On the 21st day after immunization, blood was collected and serum was isolated, and an antibody titer of the serum was determined by a microagglutination test method; the strain was used for challenge experiment on the leg muscle by intramuscular injection (a viable count was about 1.0×10⁵ CFU). The incidence and death of experimental ducks were observed. The antibody test results show that the immunized group 5/5 is greater than or equal to 1:32, and the control group 5/5 is less than or equal to 1:4; the results of challenge protection efficiency show that the immunized group 5/5 shows protection, and the control group 5/5 shows incidence.

Example 4: Preparation of Antigens of a *Salmonella typhimurium* S01 Strain, a *Riemerella anatipestifer* R01 Strain and an *Escherichia coli* E01 Strain 1. Cultivation of Bacterial Solution
1.1. Cultivation of a *Salmonella typhimurium* S01 strain: the S01 strain was cultivated using a fermenter: an LB medium was added at 60-80% of a volume of the fermenter, an antifoaming agent was added, and high-pressure steam was introduced for sterilization; when a temperature dropped to 37-38° C., a 1% secondary seed solution was added for fermentation culture. The fermentation culture was conducted at 36-37° C., 100 r/min and a pH value of 7.2-7.4, and dissolved oxygen content was controlled to 60-80% by adjusting an air intake during the whole culture; after 4 h of culture, sampling was conducted on the bacterial solution for viable counting and pure inspection. The fermented bacterial solution was introduced into a column centrifuge for centrifugation, and bacterial sludges were collected and stored at 2-8° C. for no more than 24 H.

1.2. Cultivation of a *Riemerella anatipestifer* R01 strain: the R01 strain was cultivated using a fermenter: a TSB medium was added at 60-80% of a volume of the fermenter, an antifoaming agent was added, and high-pressure steam was introduced for sterilization; when a temperature dropped to 37-38° C., a 1% secondary seed solution was added for fermentation culture. The fermentation culture was conducted at 36-37° C., 100 r/min and a pH value of 7.2-7.4, and dissolved oxygen content was controlled to 60-80% by adjusting an air intake during the whole culture; after 6 h of culture, sampling was conducted on the bacterial solution for viable counting and pure inspection. The fermented bacterial solution was introduced into a column centrifuge for centrifugation, and bacterial sludges were collected and stored at 2-8° C. for no more than 48 h.

1.3. Cultivation of an *Escherichia coli* E01 strain: the E01 strain was cultivated using a fermenter: an LB medium was added at 60-80% of a volume of the fermenter, an antifoaming agent was added, and high-pressure steam was introduced for sterilization; when a temperature dropped to 37-38° C., a 1% secondary seed solution was added for fermentation culture. The fermentation culture was conducted at 36-37° C., 100 r/min and a pH value of 7.2-7.4, and dissolved oxygen content was controlled to 60-80% by adjusting an air intake during the whole culture; after 4 h of culture, sampling was conducted on the bacterial solution for viable counting and pure inspection. The fermented bacterial solution was introduced into a column centrifuge for centrifugation, and bacterial sludges were collected and stored at 2-8° C. for no more than 48 h.

2. Inactivation
According to results of the viable counting, the bacterial sludges of the two strains were resuspended in an appropriate amount of a sterile physiological saline and diluted to 3.0×10⁹ CFU/ml; a 10% formaldehyde solution was added quantitatively to make a final concentration to and inactivation was conducted by stirring at 37° C. for 16 h; inactivation test was conducted, and the remaining bacteria solutions were stored at 2-8° C. for no more than 14 d.

3. Semi-Finished Product Inspection
3.1. Pure inspection was conducted according to an appendix of the current "Chinese Veterinary Pharmacopoeia".
3.2. Viable counting was conducted according to the appendix of the current "Chinese Veterinary Pharmacopoeia".

Example 5: Preparation of Vaccines

1. Antigen preparation: antigens of an E01 strain, an R01 strain and an S01 strain passed the inspection were mixed at 1:1:1 to obtain a water phase.
2. Adjuvant preparation: a Montanide™ GEL 02 adjuvant was treated at 121° C. and a high pressure for 15 min for later use.
3. Vaccine preparation: the antigens and the adjuvant were mixed in a volume ratio of 95:5.
4. Finished Product Inspection
4.1. Properties: the vaccine was a milky white homogeneous emulsion.
4.2. Inspection of filling quantity: the inspection was conducted according to an appendix of the current "Chinese Veterinary Pharmacopoeia", and results were in compliance with the regulations.
4.3. Sterility test: the test was conducted according to the appendix of the current "Chinese Veterinary Pharmacopoeia", and the result was that no bacteria should grow.
4.4. Safety inspection: 10 7-day-old cherry valley ducks were injected with 1.0 ml of vaccine into each neck muscle and observed for 14 d; the result was that there should be no local or systemic adverse reactions caused by the vaccine.
4.5. Efficacy test
4.5.1. Serological method: 20 7-day-old cherry valley ducks were taken (*Salmonella typhimurium* ELISA test were negative, *Riemerella anatipestifer* and *Escherichia coli* antibodies were negative), where 10 ducks were injected subcutaneously with 0.5 ml of the vaccine, while the remaining 10 ducks were used as non-immune controls. On the 21st day after immunization, blood was collected from all ducks and serum was separated, and antibody titer was detected for *Salmonella typhimurium*, *Riemerella anatipestifer* and *Escherichia coli*, respectively. Microagglutinated antibodies of the *Salmonella typhimurium:* 10 ducks in the immunized group all had an antibody titer of ≥1:32, and 10 ducks in the control group all had an antibody titer of ≤1:4; microagglutinated antibodies of the *Riemerella anatipestifer:* 10 ducks in the immunized group all had an antibody titer of ≥1:32, and 10 ducks in the control group all had an antibody titer of ≤1:4. Microagglutinated antibodies of the *Escherichia coli:* 10 ducks in the immunized group all had an antibody titer of ≥1:32 and 10 ducks in the control group all had an antibody titer of ≤1:4.
4.5.2. Immune challenge method: 60 7-day-old cherry valley ducks (*Salmonella typhimurium* ELISA test were negative, *Riemerella anatipestifer* and *Escherichia coli* antibodies were negative) were divided into 6 groups A, B, C, D, E and F, where groups A, B and C were injected subcutaneously with 0.5 ml of the vaccine per duck, and the remaining groups D, E and F were used as non-immune controls. On 21 days after immunization, blood was collected from all ducks and serum was separated; a challenge test was conducted, where the test ducks of groups A and D were injected intramuscularly with 1.0 ml of a bacterial solution of the S01 strain (viable count was about 1×10⁸ CFU/duck); the test ducks of groups B and E were injected intramuscularly with 1.0 ml of a bacterial solution of the R01 strain (viable count was about 1×10⁷ CFU/duck); and the test ducks of groups C and F were injected intramuscularly with 1.0 ml of a bacterial solution of the E01 strain (viable count was about 1×10⁵ CFU/duck). The incidence and death of test ducks were observed for 14 days. *Salmonella typhimurium*: at least 9 ducks in the immunized group were protected, and at least 9 ducks in the control group were diseased; *Riemerella anatipestifer*: at least 9 ducks in the immunized group were protected, and at least 9 ducks in the control group were diseased; *Escherichia coli*: at least 9 ducks in the immunized group were protected, and at least 9 ducks in the control group were diseased.

5. Vaccine Comparison Test 10, 10 and 30 cherry valley ducks were immunized using an inactivated vaccine of *Salmonella typhimurium*, an inactivated vaccine of *Riemerella anatipestifer* and the inactivated triple vaccine of *Salmonella typhimurium*, *Riemerella anatipestifer* and *Escherichia coli* of the present disclosure, respectively, while another 30 cherry valley ducks were set as unimmunized control ducks. Immunization was conducted according to an immunization schedule of each vaccine, and then challenge experiment was conducted after the immunization. The results of the challenge protection test show that, the inactivated vaccine of *Salmonella typhimurium* and the inactivated vaccine of *Riemerella anatipestifer* on the market have a relatively poor efficacy than the inactivated triple vaccine of *Salmonella typhimurium*, *Riemerella anatipestifer* and *Escherichia coli* of the present disclosure. The experimental results are shown in Table 1.

TABLE 1

Results of challenge protection efficiency of three inactivated vaccines

| Groups | Amount (duck) | Challenge protection efficiency | | |
|---|---|---|---|---|
| | | *Salmonella typhimurium* | *Riemerella anatipestifer* | *Escherichia coli* |
| Inactivated vaccine of *Salmonella typhimurium* | 10 | 8/10 | / | / |
| Inactivated vaccine of *Riemerella anatipestifer* | 10 | / | 8/10 | / |
| Inactivated triple vaccine of *Salmonella typhimurium*, *Riemerella anatipestifer* and *Escherichia coli* | 30 | 9/10 | 9/10 | 10/10 |
| Challenge control group | 30 | 9/10 incidence | 9/10 incidence | 9/10 incidence |

What is claimed is:

1. An inactivated triple vaccine for diseases in a duck caused by *Salmonella typhimurium, Riemerella anatipestifer* and *Escherichia coli*, comprising antigens and an adjuvant, wherein the antigens are an inactivated *Salmonella typhimurium* S01 strain with a deposit number of CCTCC No. M2020515, an inactivated *Riemerella anatipestifer* R01 strain with a deposit number of CCTCC No. M2020516 and an inactivated *Escherichia coli* E01 strain with a deposit number of CCTCC No. M2020514.

2. The inactivated triple vaccine for diseases in the duck caused by *Salmonella typhimurium, Riemerella anatipestifer* and *Escherichia coli* according to claim 1, wherein the antigens are inactivated by formaldehyde.

3. The inactivated triple vaccine for diseases in the duck caused by *Salmonella typhimurium, Riemerella anatipestifer* and *Escherichia coli* according to claim 1, wherein a preparation method comprises the following steps:

1) Antigen preparation: resuspending bacterial sludges of antigens of purely qualified SOL R01 and E01 strains in a proper amount of sterilized physiological saline, conducting dilution and inactivation; after passing quality inspection, mixing the three antigens at a volume ratio of 1:1:1 to obtain a mixed antigen for later use;

2) mixing the mixed antigen with the adjuvant, and stirring at a low speed evenly with a mixer; and 3) sub-packaging a mixture obtained in step 2) and capping and sealing labeling and storing at 2-8° C.

* * * * *

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: synthetic P1

<400> SEQUENCE: 1
tcgcaccgtc aaaggaaccg taaagc        26

<210> SEQ ID NO 2
<211> LENGTH: 26
<212> TYPE: DNA
<213> ORGANISM: Artificial Sequence
<220> FEATURE:
<223> OTHER INFORMATION: synthetic P2

<400> SEQUENCE: 2
gcattatcga tcagtaccag ccgtct        26

<210> SEQ ID NO 3
<211> LENGTH: 20
<212> TYPE: DNA
<213> ORGANISM: Artificial Sequence
<220> FEATURE:
<223> OTHER INFORMATION: synthetic F

<400> SEQUENCE: 3

```
acttcaggta cccccagctt                                                    20

<210> SEQ ID NO 4
<211> LENGTH: 20
<212> TYPE: DNA
<213> ORGANISM: Artificial Sequence
<220> FEATURE:
<223> OTHER INFORMATION: synthetic R

<400> SEQUENCE: 4
gtgccgtgag gtgttaggtt                                                    20
```